(12) United States Patent
Narasimhamoorthy et al.

(10) Patent No.: US 11,363,777 B2
(45) Date of Patent: Jun. 21, 2022

(54) **ROSEMARY (*ROSMARINUS OFFICINALIS* L.) DENOMINATED KI1005**

(71) Applicant: KEMIN INDUSTRIES, INC., Des Moines, IA (US)

(72) Inventors: Brindha Narasimhamoorthy, West Des Moines, IA (US); John A. Greaves, Ankeny, IA (US); Liuqing Zhao, Zhuhai (CN); Zhiqiang Qiu, Zhuhai (CN); Justin Cox, Canyon, TX (US); John Baker, Amarillo, TX (US)

(73) Assignee: KEMIN INDUSTRIES, INC., Des Moines, IA (US)

( * ) Notice: Subject to any disclaimer, the term of this patent is extended or adjusted under 35 U.S.C. 154(b) by 0 days.

(21) Appl. No.: 16/864,057

(22) Filed: Apr. 30, 2020

(65) Prior Publication Data

US 2020/0344969 A1 Nov. 5, 2020

Related U.S. Application Data

(60) Provisional application No. 62/840,756, filed on Apr. 30, 2019.

(51) Int. Cl.
*A01H 6/50* (2018.01)
*A61K 36/53* (2006.01)
*A01H 5/10* (2018.01)

(52) U.S. Cl.
CPC .............. *A01H 6/508* (2018.05); *A01H 5/10* (2013.01)

(58) Field of Classification Search
None
See application file for complete search history.

(56) References Cited

U.S. PATENT DOCUMENTS 6,450,935 B1 * 9/2002 Haworth ............ B01D 11/0288
554/21

OTHER PUBLICATIONS

Del Bano et al, 2003, J. Agric. Food Chem., 51:4247-4253.*

* cited by examiner

*Primary Examiner* — Jason Deveau Rosen
(74) *Attorney, Agent, or Firm* — Nyemaster Goode P.C.

(57) ABSTRACT

The present invention relates generally to a rosemary plant and, more specifically, to a proprietary clonal plant line KI1005 that hyper-accumulates carnosic acid.

20 Claims, 7 Drawing Sheets

ROSEMARY (*ROSMARINUS OFFICINALIS* L.) DENOMINATED KI1005

RELATED APPLICATION

This application claims the benefit of priority to U.S. Patent Application Ser. No. 62/840,756, filed Apr. 30, 2019, entitled "ROSEMARY (ROSMARINUS OFFICINALIS L.) DENOMINATED KI1005," the disclosure of which is hereby incorporated herein by reference in its entirety.

FIELD OF THE INVENTION

The present invention relates generally to a rosemary plant and, more specifically, to a proprietary clonal plant line denominated KI1005 that produces elevated levels of desirable antioxidants such as carnosic acid.

BACKGROUND OF THE INVENTION

Rosemary (*Rosmarinus officinalis* L.) is a member of the Lamiaceae family of plants, which encompasses over 500 species that have been widely used in traditional medicine. The antioxidant properties of members of the Lamiaceae family (including rosemary) have been identified within the past 4-5 decades and have demonstrated superior antioxidant activity in a variety of applications (Cuppett et al., 1997). *Rosmarinus officinalis* contains monoterpenes, sesquiterpene chemical composition, diterpenes, triterpenoids, flavonoids, fatty acids, amino acids and branched alkanes. The antioxidant activity of rosemary extract has generally been attributed to the presence of three phenolic compounds: carnosic acid (CA), carnosol (CAR) and rosmarinic acid (Cuvelier et al., 1994; Frankel et al., 1996).

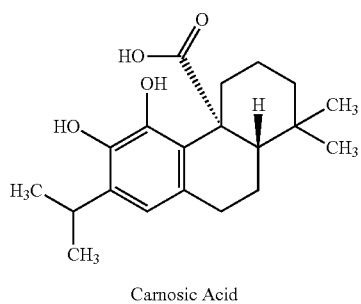

Carnosic Acid

Rosemary plants, like many other Lamiaceae family species, grown under higher temperatures, light intensity and longer day length periods tend to have increased levels of monoterpenes. The harvest time is crucial to maximize the biomass and carnosic acid concentration in rosemary. To date, progressive genetic improvement has not yet been made in the improvement of rosemary for better production of carnosic acid or other antioxidant molecules. It has been reported that wild type or naturally-occurring rosemary accumulates approximately 2-3% carnosic acid on a dry matter basis. Extraction of carnosic acid from a hyper-accumulating rosemary clonal line is crucial for producing commercially viable rosemary extract rich in carnosic acid.

The present invention, KI1005, is a proprietary rosemary clonal line with good agronomic characteristics that remarkably produces more than 7% carnosic acid, and more particularly 7.4% on average on a dry matter basis, under field conditions. KI1005 is a first-generation carnosic acid hyper-accumulating rosemary clonal plant line with substantial commercial potential.

SUMMARY OF THE INVENTION

The present invention relates to a plant or clonal line of *Rosmarinus officinalis* L. named KI1005 that has elevated carnosic acid levels, excellent vigor and overall robust agronomic traits. The present invention is an upright perennial clonal line that was developed from a rosemary breeding program at Kemin Industries.

The present invention, with elevated levels of carnosic acid and good growth habits, was selected through a robust breeding program and has been asexually propagated to produce a clonal line of identical plants.

Plants of the cultivar KI1005 have not been observed under all possible environmental conditions. The phenotype may vary somewhat with variations in environment and culture such as temperature, light intensity, day length, water status, and/or fertilizer rate or type without, however, any variance in genotype.

An object of the present invention is a plant with a high level of carnosic acid for use as an antioxidant in human and animal food, beverages and personal care products.

Another object of the invention is a variety of rosemary that is novel, stable, and uniform and has good agronomic characteristics that permit efficient cultivation of the variety as a crop that produces a high amount of biomass from which carnosic acid can be extracted.

DETAILED DESCRIPTION OF THE FIGURES

Figure 6:
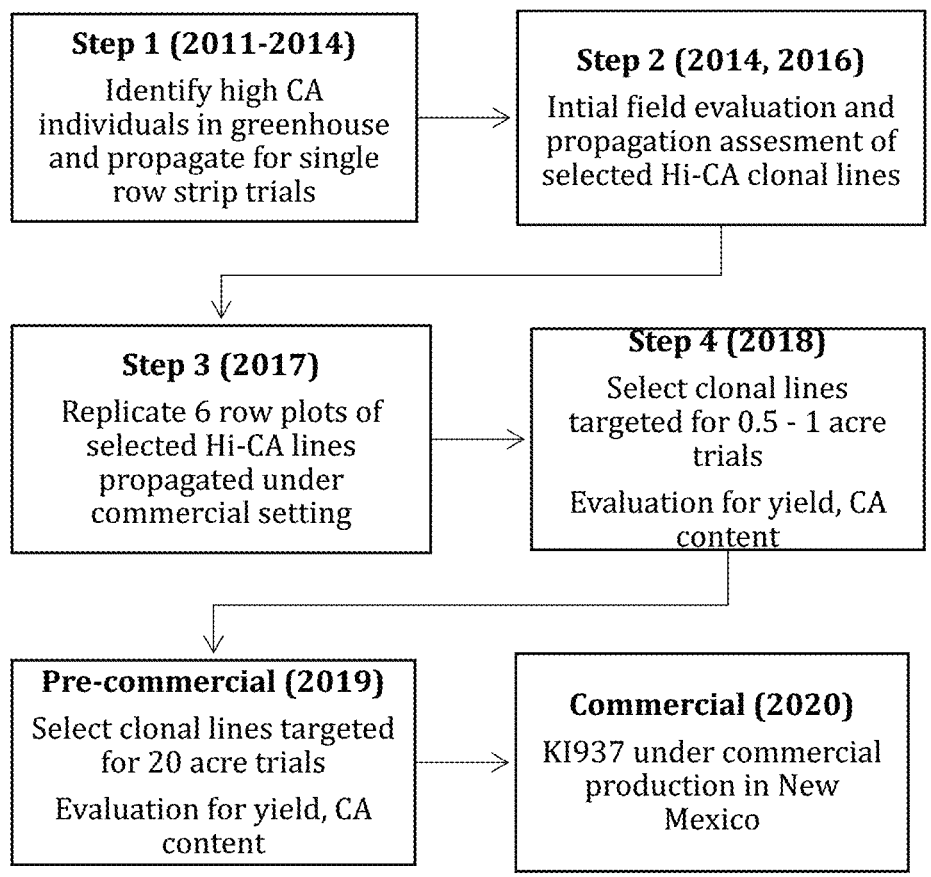

FIG. 6 summarizes the scale-up process of KI1005.

Figure 7:
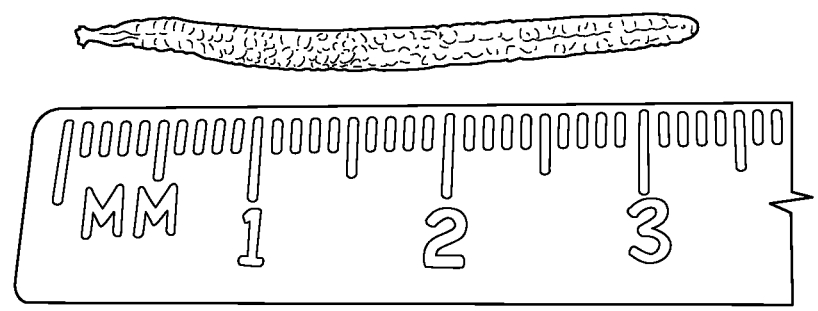

FIG. 7 shows the length of a leaf of a plant of the variety KI1005 against a centimeter scale.

Figure 8:
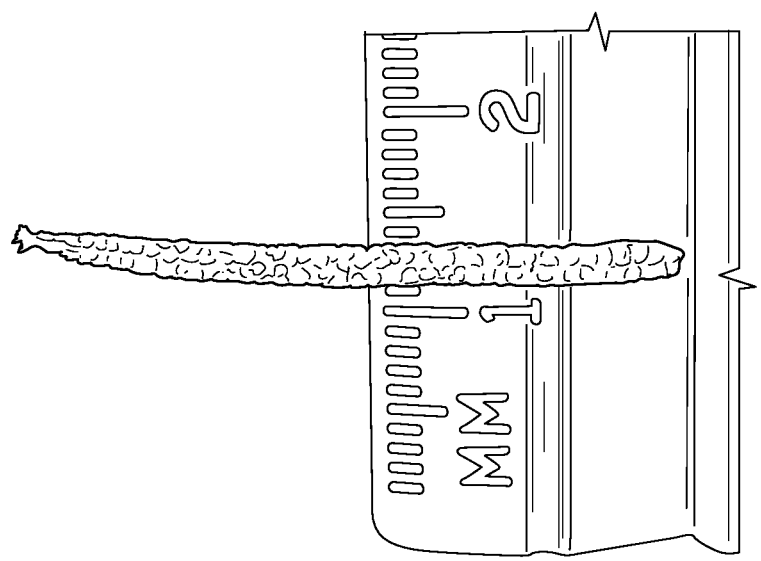

FIG. 8 shows the width of a leaf of a plant of the variety KI1005 against a centimeter scale.

Figure 9:
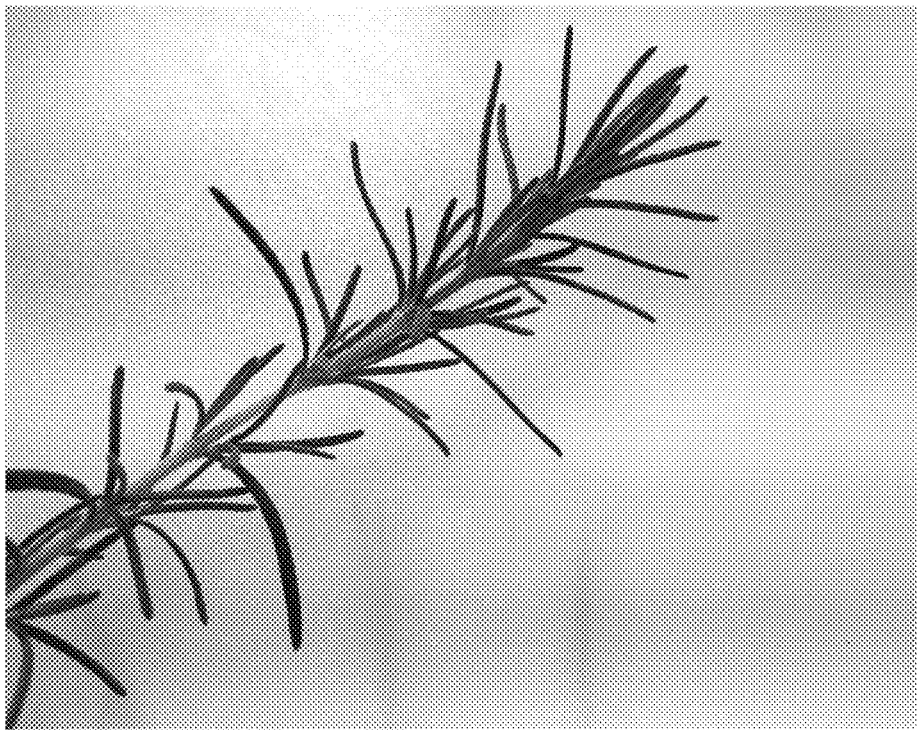

FIG. 9 shows a lateral branch of the variety KI1005.

Figure 10:

FIG. 10 shows a flowering branch of the variety KI1005.

Figure 11:
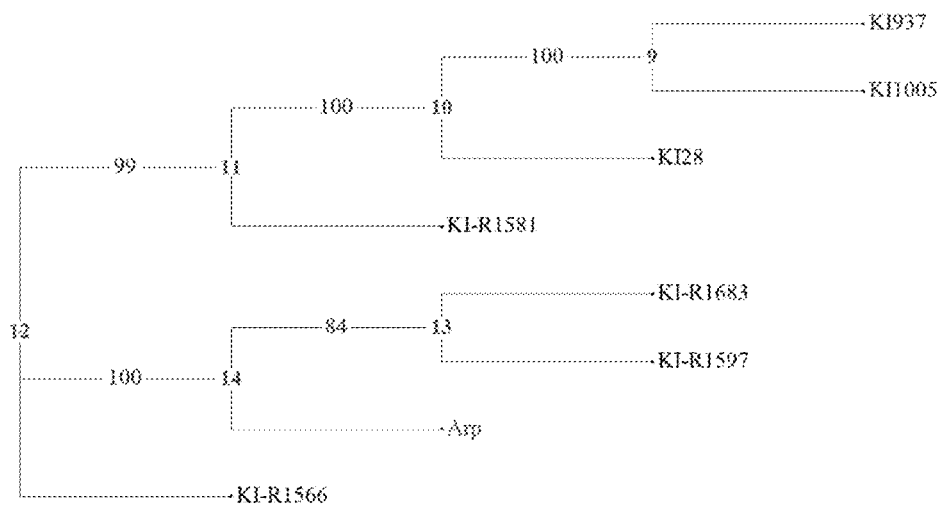

FIG. 11 depicts the phylogenetic tree based on 3068 SNPs generated by tGBS shows clustering of eight rosemary clonal lines along with public variety Arp.

Figure 12:
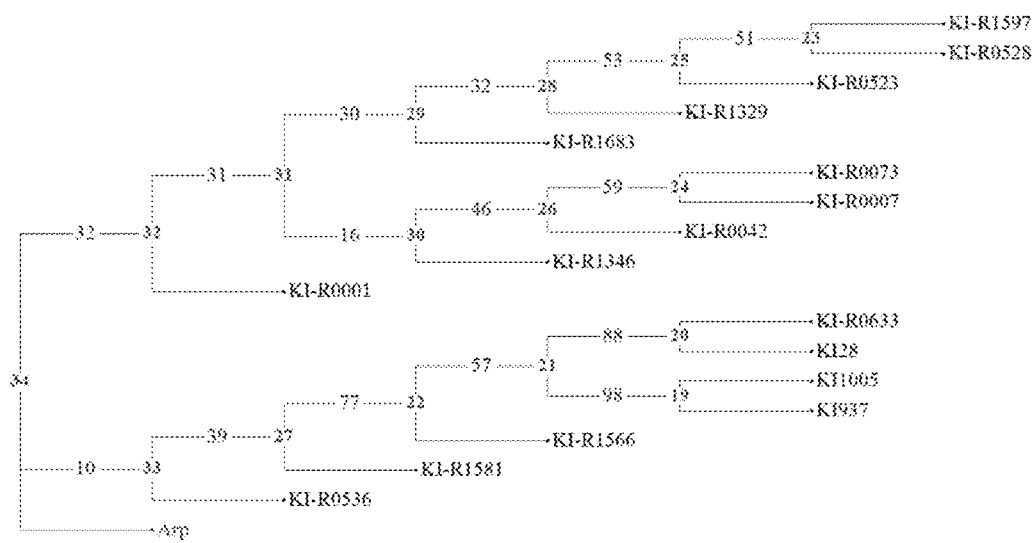

FIG. 12 depicts the phylogenetic tree based on 120 KASP marker genotype data shows clustering of Kemin proprietary rosemary clonal lines and public variety Arp.

Figure 13:
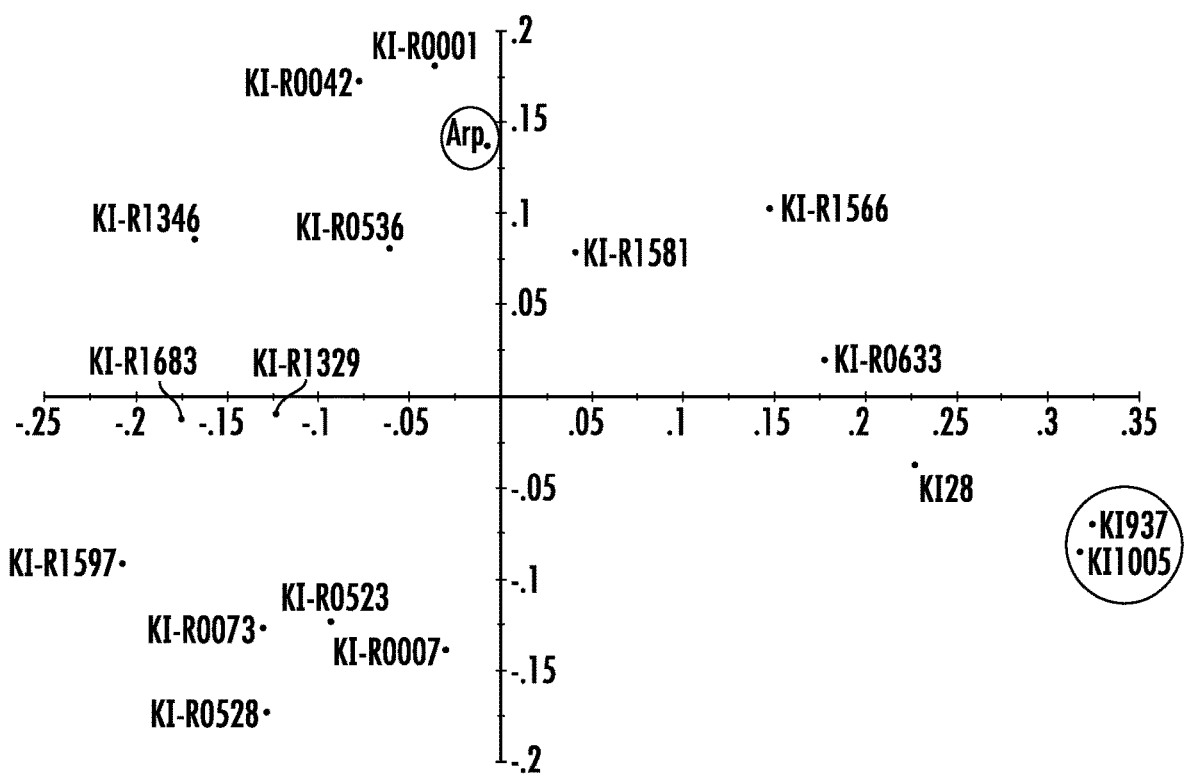

FIG. 13 represents the factorial analysis from the dissimilarity index for rosemary clonal lines using 120 KASP markers.

DETAILED DESCRIPTION OF THE INVENTION

Rosemary clonal line KI1005 is a proprietary clonal line developed through selective crossbreeding.

Methods and Materials: A crossing block containing rosemary plants obtained from Papa Geno's herb farm in Nebraska United States and plants generated from seeds obtained from publicly available sources was established at Kemin Des Moines based greenhouse. Mature flowering plants were assembled in a bee cage in October 2009. Bees were introduced to aid with pollination. Seed that represented either a self or a cross were collected from each flowering plant in the bee cage during February 2010. In addition, since dried rosemary flowers had fallen on the floor of the bee cage, seed from the floor that would still represent a self or a cross from plants within the bee case was collected.

More than 2000 seeds from the crossing block were planted in a greenhouse located on the campus of Kemin Industries, Inc. in Des Moines, Iowa. From these seeds, 380 seedlings grew well and were grown to full maturity under greenhouse conditions. When plants were 8 to 10 inches tall with a minimum of 4-5 branches, biomass from leaves and young stems representing new growth were sampled from each plant during December 2010. Leaf samples from each plant were collected at the time of maturity and air dried for CA analysis. Dry leaf samples from each line were quantitated for CA content using a previously developed method for quantitating carnosic acid on a dry mater basis.

Figure 1:
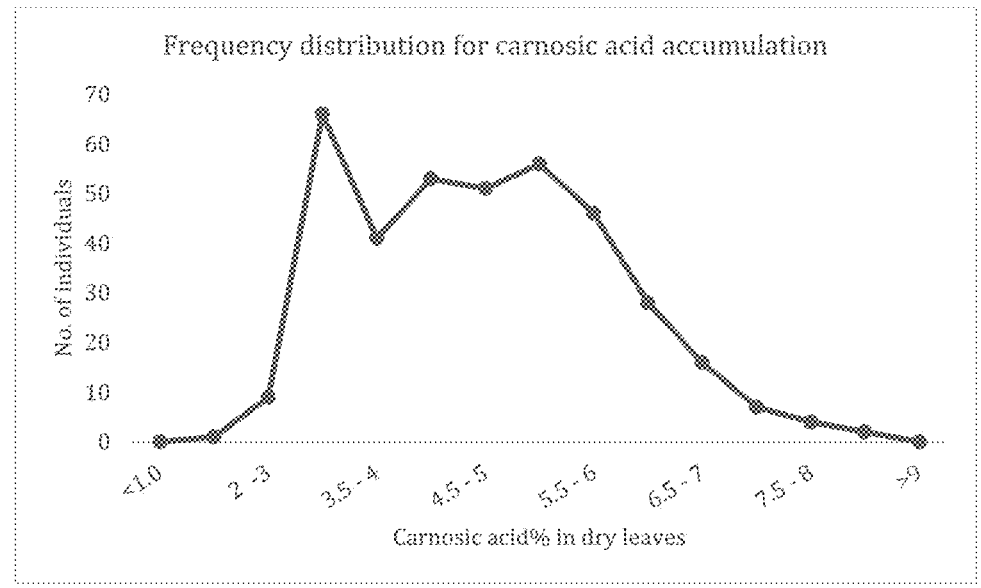
FIG. 1 depicts the frequency distribution for carnosic acid accumulation in breeding population.

A shorter HPLC assay limited to CA and CAR determination with a shorter HPLC assay time of 17 minutes suitable for screening large numbers of samples was used to analyze all the samples. Samples were prepared from each rosemary tissue and three successive extractions from the same sample were carried out. CA and CAR content were determined based on dry weight in all the samples in triplicate from both experiments. Extensive variation for carnosic acid accumulation was seen among the individuals within the population (FIG. 1).

Only twenty-nine lines with CA levels greater than 6% on dry matter basis were identified, of which only thirteen lines had CA levels higher than 7%. Most of the population was on the lower end of carnosic acid accumulation spectrum.

Figure 2:
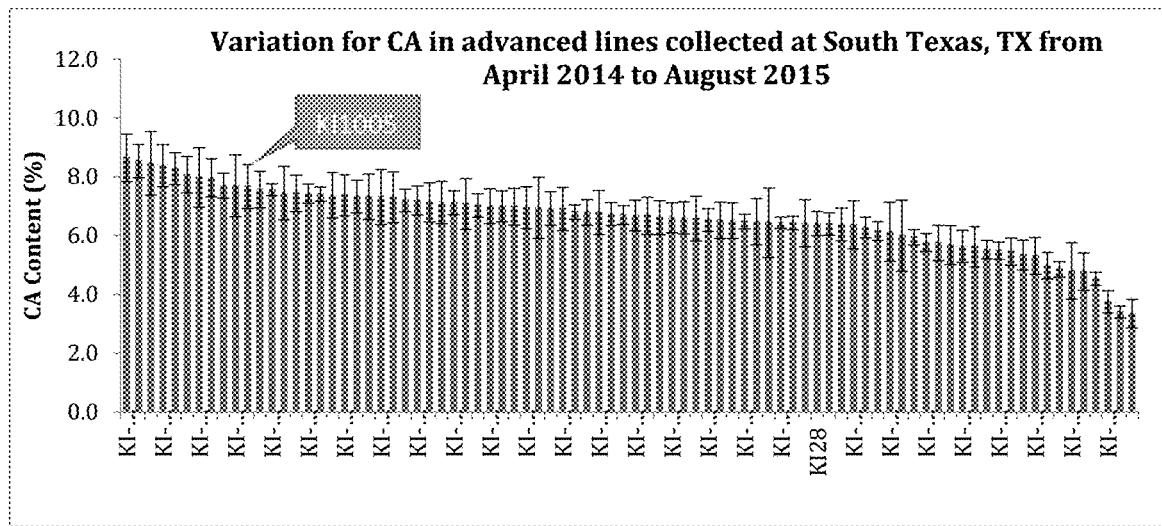
FIG. 2 depicts carnosic acid content in select lines from South Texas.

Seventy-seven lines designated as high-CA lines were selected for further field evaluation. These plants were grown in the greenhouse to allow for new growth. Cuttings were taken from each individual and dipped in rooting hormone (Dip'N Grow); and stuck in propagation trays filled with soilless mix. Propagules rooted after 8 to 10 weeks to be considered a quality plug for field transplanting. Each clonally propagated line was transplanted in 20 ft single strip rows in a field location in a south Texas, for initial field evaluation during October 2013. Adequate care including irrigation, fertilizer and weed control was given to help the propagates establish in plots. Beginning April 2014 to August 2015, leaf and stem tissue was sampled from the top 6 inches of new growth of rosemary lines established in field plots. Leaf tissue was air-dried and tested in the lab for CA content. KI1005 along with few other lines were identified as high CA accumulation lines with CA content >7.5% on dry mater basis (FIG. 2). KI1005, showed an average of 7.7±0.8% CA content throughout the sampling period in 2014 to 2015. In addition, KI1005 had a high vigor and biomass accumulation potential throughout the evaluation period, making it particularly suitable for agronomic production.

Two years after establishing the plots at South Texas excessive rains destroyed the plots. These lines were again propagated during the winter months of 2014-2015 in the Kemin greenhouse. Plugs were transplanted into 20 feet single row plots in eastern part of New Mexico state during April 2015. Adequate care including irrigation, fertilizer and weed control was given to help the propagates establish in plots.

Figure 3:
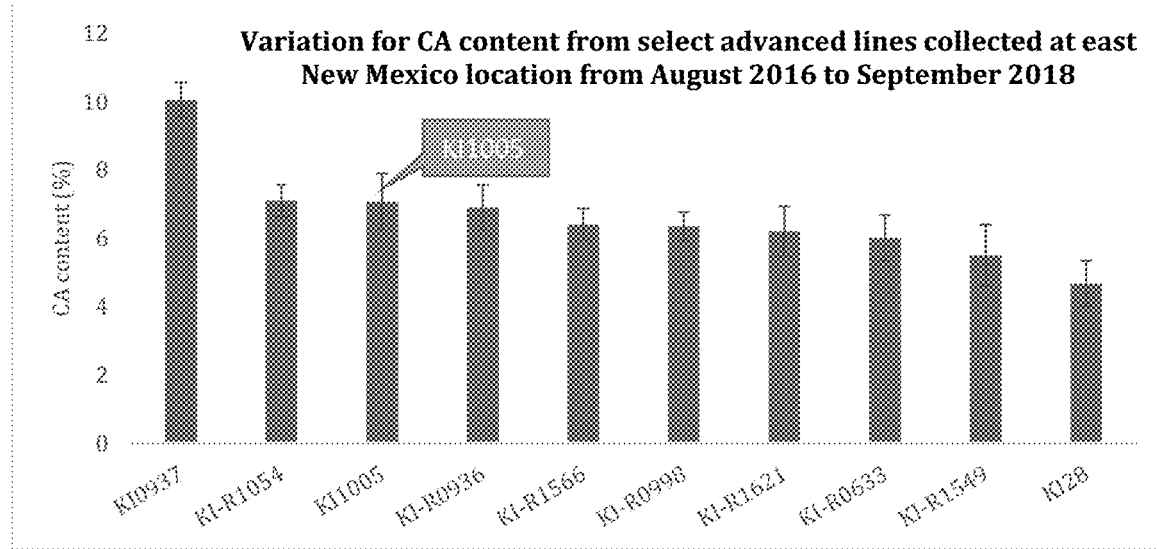
FIG. 3 depicts carnosic acid content in select lines in New Mexico.

From August 2016 to September 2018, leaf and stem tissue was sampled from the top 6 inches of new growth of the rosemary clonal lines. Biomass from selected lines were harvested at appropriate crop maturity and air-dried for CA quantitation. KI1005, KI1054 and KI937 continued to show elevated level of carnosic acid (FIG. 3). Among these lines, KI1005 exhibited much higher vigor and biomass potential compared to all other lines. The average CA levels in KI1005 was 7.1%±0.8% under field conditions.

In 2017 a subset of advanced lines was selected for further evaluation. These lines were propagated in the winter months of 2016-2017 at a commercial propagation greenhouse. Plugs were transplanted into replicated 6 rows by 15 feet plots in eastern part of New Mexico state during April 2017. Adequate care including irrigation, fertilizer and weed control was given to help the propagates establish in plots. Beginning May 2018 to September 2018, leaf and stem tissue was sampled from the top 6 inches of new growth of the rosemary clonal lines. Biomass from selected lines were harvested at appropriate crop maturity and air-dried for CA quantitation. KI1005 continued to show the elevated level of carnosic acid. The average CA levels in KI1005 was 8.5%±0.4% under field conditions.

Figure 4:
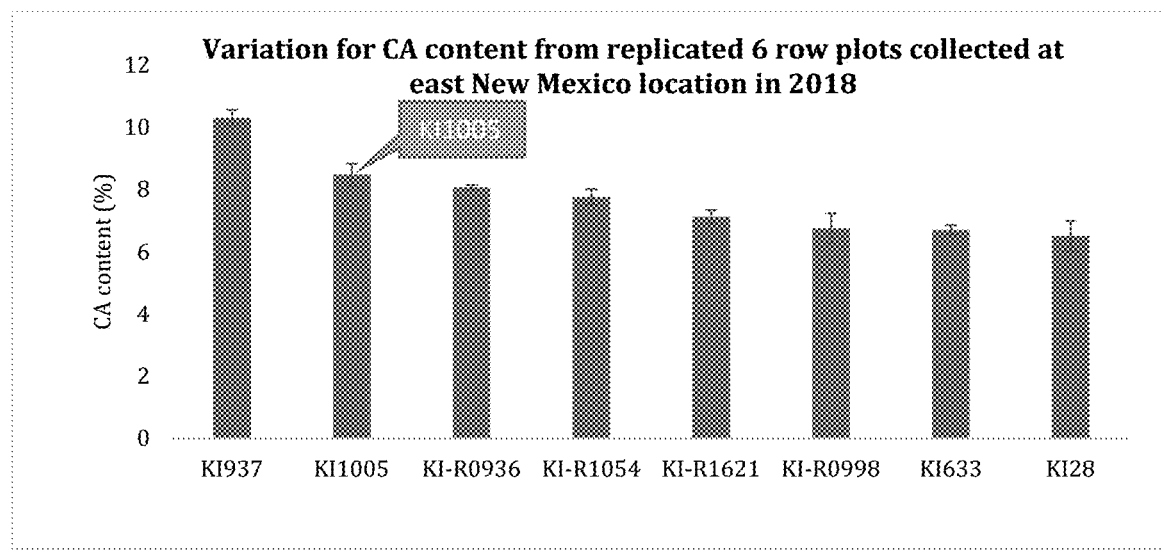
FIG. 4 depicts carnosic acid content in replicated six row plots in New Mexico.

Carnosic acid levels were generally consistent across locations. Despite the differences in growing locations, South Texas and East New Mexico, KI1005 was found to have an above average CA content in both locations (FIGS. 2, 3 and 4).

Figure 5:
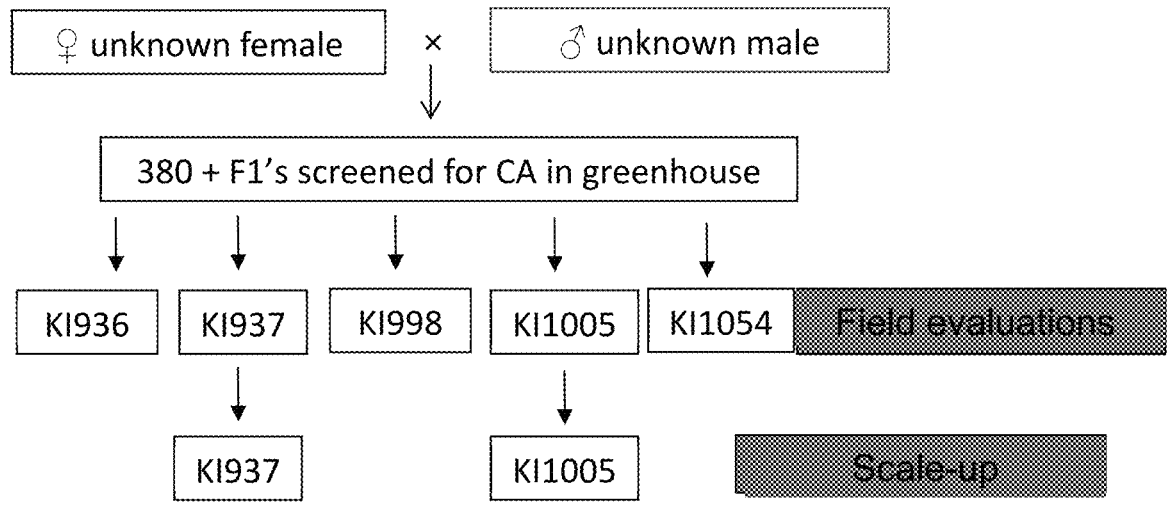
FIG. 5 shows the breeding scheme for development of KI1005.

The present invention, the plant or clonal line designated as KI1005 is a half-sib rosemary clonal line generated from a crossing block. Parental lines included in the crossing block included rosemary plants collected from publicly available rosemary accessions that were available in Papa Geno's greenhouse, North Carolina Botanical garden (NCBG) and Mullberry Creek greenhouse. However, because the seed was collected in bulk from the crossing block, identity of the specific parents from which KI1005 would have been derived is unknown; although the source lines are known (FIG. 5).

KI1005 was evaluated in single row plots for overall vigor, leaf biomass, CA yields and winter hardiness along with other lines as shown in Table 1 and Table 2. KI1005 has a consistent average winter hardiness compared to other lines in the plot. The propagation tests were conducted at the commercial propagator in New Mexico for an initial rooting assessment compared to other lines (Table 1). All lines with acceptable rooting levels in combination with elevated CA content and dry leaf biomass yields were advanced to replicated six row plots (Table 1 and Table 2).

KI1005 is a very high carnosic acid accumulating line (hyper-accumulating line) and is one of only a few to accumulate CA to this level to date. KI1005 offers an economically viable source of carnosic acid extraction and is a significant improvement over other known or commercially grown rosemary lines used for antioxidant extraction purposes.

TABLE 1

Selected advanced rosemary clonal lines for replicated plot testing

| Plant ID | Winter Hardiness 2016-2018 | Rooting Test 2016 | Average CA % 2016-2018 |
|---|---|---|---|
| KI1005 | Medium | 59% | 7.1 ± 0.8 |
| KI937 | Medium | 62% | 10 ± 0.5 |
| KI-R1597 | Medium | 90% | 8.2 ± 0.3 |
| KI-R1054 | Less | 75% | 7.1 ± 0.5 |
| KI-R0936 | Medium | 86% | 6.9 ± 0.7 |
| KI-R1566 | Excellent | 90% | 6.4 ± 0.5 |
| KI-R0998 | Good | 50% | 6.3 ± 0.4 |
| KI-R0633 | Good | 30% | 6.2 ± 0.7 |
| KI-R1621 | Medium | 91% | 6.2 ± 0.7 |
| KI-R1549 | Excellent | 90% | 5.5 ± 0.9 |
| KI28 | Medium | 48% | 4.7 ± 0.7 |

TABLE 2

Biomass and CA yield of selected advanced rosemary clonal lines

| | Estimated Dry Leaf (Kg/Acre) | | | Estimated CA Yield (Kg/Acre) | | |
|---|---|---|---|---|---|---|
| Plant ID | 2016 | 2017 | 2018 | 2016 | 2017 | 2018 |
| KI1005 | 518 | 271.4 ± 43 | 1175.6 ± 255.8 | 39.2 | 16.3 ± 2.6 | 92.1 ± 20 |
| KI937 | 395.9 | 191.6 ± 76.3 | 714.3 ± 138.7 | 39.6 | 19.1 ± 7.6 | 73.2 ± 14.5 |
| KI-R1597 | 709.3 | — | 1285.6 ± 219.9 | 55.2 | — | 108.6 ± 18.2 |
| KI-R1054 | 520.6 | 212.7 ± 5.5 | 985.3 ± 121.2 | 38.1 | 13.7 ± 0.4 | 72.2 ± 8.8 |
| KI-R0936 | 374.5 | 257.7 ± 36.2 | 962.7 ± 190.8 | 26.5 | 18.3 ± 2.5 | 71.7 ± 14.4 |
| KI-R1566 | — | 578.6 ± 95.3 | 1956.5 ± 263.6 | — | 35.4 ± 5.7 | 133.7 ± 18.1 |
| KI-R0998 | 511.2 | 355.3 ± 49.8 | 1287.7 ± 164.8 | 30.7 | 22 ± 3 | 88.6 ± 11.2 |
| KI-R0633 | 528.3 | 359.9 ± 74.2 | 1382.2 ± 215.3 | 32.6 | 19.3 ± 4 | 94.2 ± 14.6 |
| KI-R1621 | 598.6 | 211.9 ± 76 | 1089.6 ± 231 | 38.5 | 11.9 ± 4.3 | 71.8 ± 15.3 |
| KI-R1549 | — | 1172.3 ± 298.9 | 2964.2 ± 181.5 | — | 62.5 ± 15.1 | 181.5 ± 11.1 |
| KI28 | 392.5 | 236.1 ± 58.2 | 949.3 ± 89.1 | 16.3 | 11.4 ± 2.9 | 51.8 ± 4.8 |

KI1005 was evaluated in replicated 6 rows by 15 plant plots for CA content and leaf biomass. KI1005 for the 2018 season showed elevated CA content and above average dry leaf biomass. Combination of higher carnosic acid content combined with high biomass makes KI1005 as a highly desirable line since it produces a very high average CA yield on a per acre basis under field conditions (Table 3).

TABLE 3

Selected advanced rosemary clonal lines for replicated 6 row plot testing

| Plant ID | Average CA % - 2018 Season | Estimated Dry Leaf Biomass (Kg/Acre) - 2018 Season | Estimated CA Yield (Kg/Acre) - 2018 Season |
|---|---|---|---|
| KI1005 | 8.5 ± 0.4 | 1286.9 ± 217.6 | 107.2 ± 17.7 |
| KI-R1621 | 7.1 ± 0.2 | 1465.9 ± 148.4 | 105.5 ± 10.5 |
| KI-R0998 | 6.7 ± 0.5 | 1255.8 ± 167.2 | 86.6 ± 11.1 |
| KI-R0936 | 8.1 ± 0.1 | 1046.4 ± 155.4 | 84.3 ± 12.5 |
| KI28 | 6.5 ± 0.5 | 1284.3 ± 150.4 | 83.1 ± 10 |
| KI633 | 6.7 ± 0.1 | 1094.3 ± 143.9 | 73.6 ± 9.6 |
| KI-R1054 | 7.8 ± 0.3 | 740.3 ± 80.9 | 58.2 ± 6.1 |

Based on the above, KI1005 was identified for large scale planting beginning 2019 (FIG. 6). Rosemary cuttings for propagation were taken from the field during the growing season and then increased in the commercial propagation greenhouse. Additional care is required for propagules taken from the field which are typically slower rooting and heavier disease load compared to greenhouse sourced as plants.

The successful propagation of KI1005 has improved with time as professional greenhouse growers modify the propagation protocol to achieve >80% rooting to finished plug for both sources.

Phenotypic descriptions of traits required for observation are provided in Table 4. Phenotypic characteristics of KI1005 are provided in Table 5 and FIGS. 7-10 provide visual confirmation for phenotypic characteristics of KI1005.

TABLE 4

Description of the traits for KI1005 collected in greenhouse

| Trait | Description |
|---|---|
| Days to first flowering | Number of days from transplanting to when the first spike/inflorescence emerges |
| Plant height (cm) | Length of the middle stem at the time of flowering |
| Length of lateral branches (cm) | Length /Ht of the lateral stems |
| Number of lateral branches | Count on the number of lateral branches |
| Number of nodes on the middle stem | Count on the number of nodes of the middle stem |
| Internode length on the middle stem | Measure the length between $9^{th}$ and $10^{th}$ internode of the middle stem |
| Number leaves on the middle stem | Count the number of spikes per plant |
| Leaf width | taken from the fully opened leaf from $10^{th}$ node of the middle stem |
| Leaf length | taken from the fully opened leaf from $10^{th}$ node of the middle stem |
| Leaf area (cm$^2$) | Taken from the fully opened leaf from $10^{th}$ node of the middle stem |
| Leaf to stem ratio | Leaves separated from stem and weighed to obtain ratio |

TABLE 4-continued

Description of the traits for KI1005 collected in greenhouse

| Trait | Description |
|---|---|
| Carnosic acid content | Top 6 inches of the plant cut & air dried for 48 hours for carvacrol quantitation |
| Estimated dried biomass per acre | Actual dried biomass obtained from 1 m2 area and estimated on a per acre basis |

TABLE 5

Phenotypic characteristics of KI1005 observed in the greenhouse

| Trait | Average | Range |
|---|---|---|
| Days to first flowering from date of transplanting rooted | 260 | 240-300 |
| Plant height (cm) | 50 cm | 40-60 cm |
| Length of lateral branches (cm) | 37.5 cm | 30-45 cm |
| Number of lateral branches | 20 | 15-25 |
| Number of nodes on the middle stem | 21.5 | 15-28 |
| Internode length on the middle stem | 1.8 cm | 1.7-1.9 cm |
| Number of leaves on the middle stem | 43 | 30-56 |
| Leaf width | 0.25 cm | 0.2-0.3 cm |
| Leaf length | 2.8 cm | 2.3-3.3 cm |
| Leaf area (cm$^2$) | 0.72 cm$^2$ | 0.46-0.99 cm$^2$ |
| Leaf to stem ratio | 2.4 | 2.2-2.6 |
| Carnosic acid content (%) during maturity | 7.8% | 7.82-7.84% |
| Dry biomass/acre | 593.7 Kg | 275.5-900.1 Kg |

DNA Fingerprint Profile Through Single Nucleotide Polymorphism (SNPs) And KASP Markers:

In addition to phenotypic observations, the present invention can also be identified by its genotype. DNA based techniques are more powerful in identifying the genetic differences between clonal lines/varieties. The genotype of a plant can be characterized through a genetic marker profile which can identify plants of the same variety or a related variety or be used to determine or validate a pedigree. Genetic marker profiles can be obtained by techniques various techniques. SNPs are one of the most abundant DNA variants related to genotype, chemotype and phenotype found in plant genomes. SNP based marker assays are high throughput, highly reproducible and highly applicable in generating DNA fingerprints for a plant species of interest. Development of SNP markers for fingerprinting requires the following steps: (i) partial sequencing of multiple clonal lines by next-generation sequencing technologies; (ii) SNP discovery after aligning sequence reads; (iii) validate SNPs to identify true variants; and (iv) SNP genotyping of germplasm collection or populations to create a unique fingerprint based on polymorphisms. A subset of Kemin proprietary rosemary lines and publicly available rosemary clonal lines were sequenced to identify SNPs and validate them. These SNPs were converted to the KASP marker system in order to genotype Kemin's proprietary germplasm to identify true allelic variants and create a unique genetic fingerprint for each of the rosemary clonal line under investigation.

Sequencing and SNP identification. Sequencing, read quality checking, read trimming, de novo read alignment, and identification of SNPs were carried out by a third-party service provider Dat2Bio LLC in Ames, Iowa. Leaf samples of eight proprietary rosemary clonal lines and publicly available rosemary line such as 'Arp' were obtained from the Kemin greenhouse, frozen/freeze-dried and provided to Dat2Bio. The eight clonal lines were replicated 12 times to make a total 96 sequencing samples for maximum coverage of whole genome sequence. Sequencing was performed using LifeTech's Ion Proton instrument. Sequence reads were filtered using standard filtering parameters to remove the poor-quality reads and sorted with barcodes that represent individual sample. Trimmed clean reads were then used for de novo genome assembly of rosemary genome. Tunable Genotyping by Sequencing (tGBS) was used to obtain sequence information and discovery of SNPs. Two different approaches were used for SNP calling, (i) Stringent Minimum Call Rates 50% (MCR50), in which all the SNPs were identified with a ≥50% minimum call rate with an average 85 reads per SNP position, and (ii) Stringent Minimum Call Rates ≥75% (MCR75) in which ≥75% minimum call rate with an average 85 reads per SNP position were used.

The raw tGBS reads from the Ion Proton instrument were trimmed and aligned to create a de novo assembly of rosemary genome, since no prior genome information exists for rosemary. Aligned sequences were used to discover single base differences among eight clonal lines to identify SNPs, which were filtered resulting in 181,618 SNPs. From these, there were at least ~11,300 polymorphic SNPs between the present invention and Arp. From these, a set of 144 SNPs that can distinguish all the eight clonal lines was identified and KASP markers were developed for the same.

DNA extraction. All rosemary clonal lines were genotyped using 144 KASP markers. Leaf tissue collected from all the clonal lines was freeze dried and ground into fine powder in 1.5 ml Eppendorf tubes, and DNA was isolated using CTAB protocol with the following modifications. Freshly prepared 2X CTAB with 2% PVP, 0.2% Mercaptoethanol and 5 µl RNaseA was added to the ground tissue samples and immediately placed in a water bath for incubation at 65° C. for 90 mins with occasional shaking of the tubes. Equal volume of chloroform isoamylalcohol was added and shaken for 10 mins for protein precipitation followed by centrifugation at 12000 rpm for 10 mins. Supernatant was transferred into new 1.5 ml tubes and DNA was precipitated with 0.6 volume 2-propanol followed by washing DNA pellet with 75% ethanol. Air dried pellet was dissolved in RO water for KASP assays.

Development of KASP markers genotyping. A total of 3068 SNP markers were identified through the tGBS pipeline among 8 rosemary clonal lines including public variety 'Arp'. Of these 3068 SNPs, based on contig length and reliability of SNP calls, 144 KASP markers were designed and oligo-synthesized. All of the 144 KASP markers were used to assay 18 clonal lines including 8 clonal lines that were used for original tGBS genotyping.

Genotyping and data analysis. For each sample genotyping was performed in 5 µl KASP PCR reactions using Roche Light Cycler® 480 qPCR machine with 384 well plates (Roche Life technology USA). KASP PCR reactions contained 2.5 µl 2X KASP master mix (LGC Genomics), 0.08 µl primer mix (IDT, IA, USA) and 2.5 µl template DNA. Thermocycling was started with 15 min at 94° C., a touchdown phase of 10 cycles at 94° C. for 20 s and 65° C. for 60 s with a 1° C. decrease in temperature per cycle, followed by 35 cycles of 94° C. for 20 s and 55° C. for 60 s. Once the thermal cycle was complete, fluorescence signal was acquired at 520 nm (FAM) and 556 nm (HEX) at 37° C. for 10 s. Data was then analyzed using LightCycler® 480 SW 1.5.1 software (Roche Life Science, CA, USA) to identify SNP genotypes. For each marker, homozygous and heterozygous calls were made and scored as co-dominant markers.

KASP genotyping assay results were recorded as a two-letter codes i.e., AA, BB, AB or No calls. A DNA fingerprint was made using all the SNP based KASP marker genotypes. AA represents homozygous reference allele, BB represents homozygous alternate allele, AB represents heterozygous and No calls represents absence of both alleles for respective KASP marker. Phylogenetic tree and factorial analysis from the dissimilarity index were carried out using software, DarWin. Cluster analysis and factorial analysis of dissimilarity were calculated using Neighbor-Joining method. Multiple rooted phylogenetic trees were generated using DarWin software. Heatmap analysis and genetic diversity analysis were performed using software R with statistical packages heatmap and SNP ready, respectively.

A total 246,336 scaffolds were generated ranging from 30 bp to 203 bp long. An average 12,112,651 reads were achieved for each clonal line. Genome assembly of short reads generated 21,830,060 bp which was used for SNP calling using tGBS pipeline. SNP calling was performed and compared using two difference approaches, (i) Stringent Minimum Call Rates 50% (MCR50), in which all the SNPs were identified with a ≥50% minimum call rate with an average 85 reads per SNP position and (ii) Stringent Minimum Call Rates ≥75% (MCR75) was used in which a total 3068 SNPs were identified.

The eight clonal lines were clustered into two major clades based on the 3068 SNPs generated by tGBS system. Arp and the three commercial lines (KI28, KI937 and KI1005) were placed in a distinctly different clade (FIG. 11).

Cluster Analysis and phylogenetic tree construction using KASP marker data. Eighteen clonal lines were clustered into groups based on their similarities in KASP genotype data. Genotype data from a total 120 KASP markers were used for generating clades/clusters. Cluster analysis of KASP marker variation corresponded well to the SNP variation with more resolution on clusters (FIG. 12). KASP marker data clustering resulted in three distinct clades (FIG. 12). Arp was distinctly different from all the lines and formed its own clade. The second clade consisted of various sub-clusters, of which KI937 and KI1005 formed a sub-sub-cluster. Greater level of similarity between KI28 and KI633 clustered them together, and relatively closer to KI1005 and KI937. The first clade generally consisted of commonly available rosemary lines such as KI-R0001 (public name Nancy Howard), KI-R007 (public name Pine Scented), KI-R0042 (public name Hulka) and KI-R0073 (public name Baby PJ rosemary) along with a few Kemin breeding lines, and further divided into three sub clusters. KI-R0001 formed a distinct sub-clade within the first clade. Three other public varieties (KI-R0007, KI-R0042, KI-R0073), along with a breeding line KI1346 formed a sub-cluster within the first clade.

Similarity coefficients of genetic distance between clonal lines ranged from −0.02 to 0.35 (FIG. 11). The greatest degree of dissimilarity was observed between Arp and KI1005 (FIG. 13).

A SNP and KASP marker profile/genetic fingerprint were created for each of the Kemin rosemary germplasm. Due to the inherent genetic differences, Kemin's proprietary rosemary lines were distinctly grouped into specific clades. More importantly, a distinct DNA-based marker profile for KI1005 in comparison with the publicly available and commercially grown clonal line Arp has been created. A set of KASP markers were identified that can differentiate KI1005 from Arp is shown in Table 6.

TABLE 6

KASP marker genotype data distinguish Arp from KI1005 and other lines

| KASP Markers | KI28 | KI937 | KI1005 | Arp |
|---|---|---|---|---|
| P24 | AA | AA | AA | AB |
| P34 | BB | AA | AA | AB |
| P47 | BB | BB | AA | AB |
| P53 | AB | BB | BB | AA |
| P58 | AB | AA | AA | BB |
| P62 | BB | BB | BB | NA |
| P63 | AB | AB | AB | AA |
| P66 | AA | AB | AB | AA |
| P71 | NA | BB | BB | NA |
| P72 | AA | AB | AB | AA |
| P75 | AA | BB | AA | AB |
| P76 | AB | AB | AB | BB |
| P77 | AB | AB | AB | BB |
| P78 | AA | AB | AB | AA |
| P79 | BB | AB | AB | BB |
| P80 | BB | BB | BB | AB |
| P83 | AB | AB | AA | BB |
| P84 | AB | AB | AA | BB |
| P92 | AA | AA | AA | AA |
| P103 | AA | AB | AB | AA |
| P108 | AA | AB | AB | AA |
| P115 | AA | AB | AB | AA |
| P116 | AA | AB | AB | AA |
| P118 | AA | NA | AA | AB |
| P123 | AB | BB | BB | AA |
| P129 | AA | AA | AA | AB |
| P131 | AA | AA | AA | AB |
| P138 | BB | AB | AB | BB |

The occurrence of high carnosic acid accumulating lines with the DNA marker profile, such as described herein, are exceedingly rare. The few known rosemary plants capable of producing carnosic acid levels in leaf tissue (e.g., greater than 5% carnosic acid on a dry weight basis) die within a few months. In contrast, the present invention, plant or clonal line denominated KI1005, has survived for four years in the field and its vigor and biomass is equivalent to other commercial varieties.

According to at least one embodiment of the present invention, the rosemary plant leaf tissue contains at least 7% carnosic acid, for instance about 7.1, 7.3, 7.5 or 7.7% carnosic acid on a dry weight basis.

In another embodiment, the rosemary plant leaf tissue contains up to three times the amount of carnosic acid compared to known rosemary plants that may range from 0.5% to 7% carnosic acid on a dry weight basis.

The present invention is a unique, genetically distinct and stable clonal line, capable of accumulating about 7% or more carnosic acid during the active growing season, under field conditions. In contrast to the present invention, the average level of carnosic acid observed in an unselected population of rosemary is about 3% on a dry matter basis; the average level of carnosic acid observed in another commercial line, KI28, is about 5.5% on average on a dry matter basis under field conditions. Combined with good growth habits and biomass, KI1005 is a unique and highly desirable biomass source for carnosic acid extraction.

Evidence of Uniformity and Stability

No variants of any kind have been observed since the variety KI1005 was identified, indicating the stability and uniformity of the genotype. It is clear from these results that the KI1005 cultivar is stable and reproduces true to type in successive generations of asexual reproduction.

Statement of Distinction

KI1005 consistently produces higher per dry weight levels of carnosic acid as compared to other selected and commercial varieties, for instance up to fifteen times the amount of carnosic acid on a dry weight basis, while its vigor and biomass is equivalent to other commercial varieties. Due to vigorous vegetative growth this genotype can be harvested multiple times in a season and has the potential of growing in any temperate climate.

Deposit Information

Applicant made a deposit of rosemary plant line KI1005 with the Provasoli-Guillard National Center for Marine Algae and Microbiota, Bigelow Laboratory for Ocean Science, 60 Bigelow Drive, East Boothbay, Me. 04544, assigned Accession Number 201909054, from which plants of rosemary plant line KI1005 can be reproduced. The biological tissue was deposited on Sep. 24, 2019 and was obtained from the line maintained by Kemin Industries, Inc., 1900 Scott Avenue, Des Moines, Iowa 50317, since prior to the filing date of this application. Access will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R. § 1.808. This deposit of rosemary plant line KI1005 will be maintained the National Center for Marine Algae and Microbiota, which is a public depository, for a period of 30 years, or 5 years after the most recent request, or for the enforceable life of the patent, whichever is longer, and will be replaced if it becomes nonviable during that period. Additionally, Applicant has or will satisfy all of the requirements of 37 C.F.R. §§ 1.801-1.809, including providing an indication of the viability of the sample upon deposit. Applicant has no authority to waive any restrictions imposed by law on the transfer of biological material or its transportation in commerce. Applicant does not waive any infringement of rights granted under this patent or under the Plant Variety Protection Act (7 U.S.C. § 2321 et seq.).

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

The foregoing description has been presented for the purposes of illustration and description. It is not intended to be an exhaustive list or limit the invention to the precise forms disclosed. It is contemplated that other alternative processes and methods obvious to those skilled in the art are considered included in the invention. The description is merely examples of embodiments. It is understood that any other modifications, substitutions, and/or additions may be made, which are within the intended spirit and scope of the disclosure. From the foregoing, it can be seen that the exemplary aspects of the disclosure accomplishes at least all of the intended objectives.

The invention claimed is:

1. A method of producing carnosic acid, comprising extracting carnosic acid from plant tissue of a rosemary plant denominated KI1005 as produced by a rosemary line deposited with the National Center for Marine Algae and Microbiota and assigned Accession Number 201909054.

2. The method of claim 1, wherein the plant tissue is selected from the group consisting of leaf, rhizome, root, seed, or stem tissue.

3. The method of claim 1, further comprising using the extracted carnosic acid as an antioxidant in a product selected from the group consisting of human food, animal food, beverages and personal care products.

4. A method of providing an antioxidant, comprising extracting carnosic acid from plant tissue of a rosemary plant denominated KI1005 as produced by a rosemary line deposited with the National Center for Marine Algae and Microbiota and assigned Accession Number 201909054.

5. The method of claim 4, wherein the antioxidant is included in product selected from the group consisting of: human food, animal food, beverages and personal care products.

6. A method of providing an antioxidant, comprising:
   a. growing a rosemary plant denominated KI1005 as produced by a rosemary line deposited with the National Center for Marine Algae and Microbiota and assigned Accession Number 201909054;
   b. harvesting plant tissue of the rosemary plant;
   c. extracting carnosic acid from the plant tissue; and
   d. using the carnosic acid in a product.

7. The method of claim 6, wherein the tissue is selected from the group consisting of leaf, rhizome, root, seed, or stem tissue.

8. The method of claim 6, wherein the product is selected from the group consisting of human food, animal food, beverages and personal care products.

9. The method of claim 6, wherein the plant tissue comprises at least 9% carnosic acid on a dry weight basis after the plant material is dried.

10. A method by which the rosemary plant line denominated KI1005 is used in a breeding program by using pollen from said clonal lines as a male parent; or flowers of KI1005 as a female parent, for the generation of seed of a breeding population from which further selections can be made.

11. A plant or node of the rosemary plant line denominated KI1005, or a cutting or part thereof, wherein representative plant tissue of KI1005 has been deposited with the National Center for Marine Algae and Microbiota and assigned Accession Number 201909054.

12. The plant of claim 11, wherein the plant or part thereof includes a leaf, rhizome, root, seed, or stem tissue.

13. The plant or node of claim 11, wherein the plant, node, cutting or part of the plant is a starting material to grow or propagate additional plants.

14. Pollen of the plant of claim 11.

15. An ovule of the plant of claim 11.

16. A method for producing rosemary seed, said method comprising the steps of: (i) growing one or more plants from one or more of the plant or node of claim 11; (ii) pollinating one or more plants produced from one or more of the plant or node by self-pollination or by pollination with pollen from a different plant and, (iii) harvesting resultant seed, and growing a new population.

17. A rosemary plant or part thereof, having the physiological, morphological characteristics and DNA profile of the rosemary plant line denominated KI1005 that has been deposited with the National Center for Marine Algae and Microbiota and assigned Accession Number 201909054.

18. The rosemary plant of claim 17, wherein the plant or part thereof includes plant tissue, node, leaf, rhizome, root, seed, or stem tissue.

19. Pollen of the rosemary plant of claim 17.

20. An ovule of the rosemary plant of claim 17.

* * * * *